US012440670B2

(12) United States Patent
Ollivier

(10) Patent No.: US 12,440,670 B2
(45) Date of Patent: Oct. 14, 2025

(54) LEAD DEVICE FOR IMPROVED PUNCTURING FOR CARDIAC STIMULATION

(71) Applicant: SORIN CRM SAS, Clamart (FR)

(72) Inventor: Jean-François Ollivier, Gif-sur-Yvette (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 18/711,830

(22) PCT Filed: Sep. 30, 2022

(86) PCT No.: PCT/EP2022/077362
§ 371 (c)(1),
(2) Date: May 20, 2024

(87) PCT Pub. No.: WO2024/068000
PCT Pub. Date: Apr. 4, 2024

(65) Prior Publication Data

US 2024/0325737 A1 Oct. 3, 2024

(51) Int. Cl.
*A61N 1/05* (2006.01)
*A61N 1/362* (2006.01)

(52) U.S. Cl.
CPC .......... *A61N 1/0573* (2013.01); *A61N 1/362* (2013.01); *A61N 2001/058* (2013.01)

(58) Field of Classification Search
CPC .................................................. A61N 1/0573
See application file for complete search history.

(56) References Cited

U.S. PATENT DOCUMENTS

| | | | | |
|---|---|---|---|---|
| 7,383,091 | B1 | 6/2008 | Chitre et al. | |
| 8,406,899 | B2 | 3/2013 | Shantanu et al. | |
| 2004/0267342 | A1 | 12/2004 | Alinder | |
| 2011/0034985 | A1* | 2/2011 | Bush | A61N 1/0573 607/127 |
| 2023/0381502 | A1* | 11/2023 | Bauer | A61N 1/0575 |

OTHER PUBLICATIONS

International Search Report and Written Opinion, PCT/EP2022/077362, May 22, 2023, 10 pages.

* cited by examiner

*Primary Examiner* — Tammie K Marlen

(57) ABSTRACT

The invention relates to a lead device with improved puncturing capability and reliability. The proposed structure, shape and dimensions of a tip of the lead device are configured to enable a controlled and smooth puncturing process through the septum or other tissue at the target area with high reliability and longevity. A fixed helix is provided to facilitate handling and an additional screwing sty let with screwdriver functionality may be provided to improve torque transfer to the tip of the lead device for better control of a puncturing process.

12 Claims, 7 Drawing Sheets

LEAD DEVICE FOR IMPROVED PUNCTURING FOR CARDIAC STIMULATION

FIELD OF THE INVENTION

The invention relates to the field of lead devices (e.g., electrode catheters) for cardiac pacing systems, such as—but not limited to—left bundle branch pacing (LBBP) systems.

BACKGROUND OF THE INVENTION

The following terms and their abbreviations may be used in the present disclosure: Electrocardiogram (ECG), left ventricle (LV), right ventricle (RV), left atrium (LA), right atrium (RA), right ventricular apex (RVA) His-bundle pacing (HBP), left anterior oblique view (LAO), right anterior oblique view (RAO), left bundle branch (LBB), right bundle branch (RBB), left bundle branch pacing (LBBP), left bundle branch block (LBBB), left ventricular activation time (LVAT), right bundle branch block (RBBB), ventricular septum (VS), sinoatrial node (SAN), atrioventricular node (AVN), intraventricular septum (IVS), right ventricular outflow tract (RVOT) pacing, direct His bundle pacing (DHBP), and parahisian pacing (PHP).

Different electrical activation sequences of cardiac pacing may lead to different mechanical pump efficiencies of a stimulated heart. What is needed is a fast and homogenous contraction of heart ventricles to optimize pump efficiency.

Traditional pacing sites such as the RVA may provide a stable lead position with low displacement rate but are not very effective to optimize LV contraction (representing about 80% of the heart mass). Long-term right ventricular apical pacing may have deleterious effects on left ventricular function by inducing a iatrogenic left bundle branch block, which can have strong influences on the left ventricle hemodynamic performances. This observation led to a reassessment of traditional approaches and to a research of alternative pacing sites, in order to get to more physiological pattern of ventricular activation and to avoid deleterious effects. Attempts were made with RVOT pacing, DHBP, PHP and bifocal (RVA+RVOT) pacing.

LBBP has emerged as an alternative method for delivering physiological pacing to achieve electrical synchrony of the LV, especially in patients with infranodal atrioventricular block and/or LBBB. The proximal LBBs run through the LV septum and fan out to form a wider target for pacing compared to the His bundle. A technique for LBBP has been developed using a ventricular transseptal approach (i.e., pacing the LV from the RV). LBBP has been reported to offer low pacing thresholds and large R waves, and because the distal conduction system is targeted, has a lower theoretical risk for development of distal conduction block.

However, challenges concerning minimization of the impact of the pacing device through the septum (e.g., arteries permanent damages), downsizing and controlling the puncturing process at the septum, and ensuring long-term reliability of the pacing device exposed to septum contraction constrains remain.

SUMMARY OF THE INVENTION

It is an object of the present invention to provide an electrode catheter system that addresses the above challenges faced in connection with LBBP or other pacing approaches.

This object is achieved by a lead device as claimed in claim 1 and by a lead system as claimed in claim 8.

According to a first aspect, a lead device comprises:

a lead body; and a lead tip comprising a fixed distal helix as a first electrode and an interelectrode portion between the helix and a proximal second electrode;

wherein a ratio between a first outer diameter of the helix and a second outer diameter at a distal end of the interelectrode portion is set between 0.8 and 1, the first outer diameter is set between 1 and 1.8 mm, the length of the lead tip is set between 8 and 15 mm, and the length of the helix is set between 1.5 and 5 mm.

According to a second aspect, a lead system comprises the lead device of the first aspect and a screwing stylet configured to be insertable into the lead device and coupleable to an integrated driver of the lead tip of the lead device via a coupling end in order to transfer a torque to the helix.

Accordingly, a lead device with improved puncturing capability and reliability can be provided. The proposed dimensions of the tip of the lead device facilitates insertion of the interelectrode portion into the tissue at the target area to enable a controlled and smooth puncturing process through the septum or other tissue with high reliability. The fixed helix facilitates handling to improve the control over the puncturing process for placement of the lead device.

According to a first option of the first or second aspect, the interelectrode portion may have a conical shape. The proposed conical shape of the interelectrode portion further facilitates insertion of the interelectrode portion into the tissue at the target area. According to a second option of the first or second aspect, which can be combined with the first option, the lead body may have a coradial structure. Thereby, a less bulky and stiff lead structure can be provided, wherein a single coil which consists of two or four parallel, alternating insulated conductor strands extends down the length of the lead device (with a central lumen to allow for insertion of a screwing stylet).

According to a third option of the first or second aspect, which can be combined with the first or second option, the interelectrode portion may comprise a screw structure molded or otherwise formed on or attached to an outer surface of the inter-electrode portion. This screw structure facilitates the puncturing process when the interelectrode portions enters the tissue at the target area.

According to a fourth option of the first or second aspect, which can be combined with any of the first to third options, a third outer diameter at the proximal second electrode may be set between 1.25 mm and 1.94 mm. This dimensional range of the outer diameter at the distal second electrode (e.g., anode) further optimizes the shape of the lead device at the tip portion to facilitate the puncturing process.

According to a fifth option of the first or second aspect, which can be combined with any of the first to fourth options, the lead tip may further comprise an integrated driver adapted to be coupleable to a coupling end of an insertable screwing stylet, wherein the helix is configured to receive a torque by means of the screwing stylet via the driver. Thereby, an additional screwing stylet with screw-driver functionality can be involved to improve torque transfer to the tip of the lead device for better control of the puncturing process.

According to a sixth option of the first or second aspect, which can be combined with any of the first to fifth options, the driver may comprise an adapter with a mating portion adapted to be coupleable to the coupling end of the screwing stylet. This measure provides the advantage that the lead device can be adapted via the adaptor to different types of screwing stylets and vice versa.

According to a seventh option of the first or second aspect, which can be combined with any of the first to sixth options, the screwing stylet may further comprise a conical portion and/or a reduced diameter portion at the coupling end to increase flexibility. Thereby, insertion of the screwing stylet into the inserted lead device can be facilitated in curvy portions.

According to an eighth option of the first or second aspect, which can be combined with any of the first to seventh options, the lead device may be configured to allow an elastic elongation of the lead body to generate a compression force to support engagement of the coupling end into the driver. Thereby, a strong and reliable coupling between the screwing stylet and the driver can be achieved.

According to a ninth option of the first or second aspect, which can be combined with any of the first to eighth options, the screwing stylet may be made of Nitinol. Nitinol is a highly elastic material which is more efficient and robust to sustain torque constrains and avoid any risk of breakage in use.

According to a tenth option of the first or second aspect, which can be combined with any of the first to ninth options, the screwing stylet may further comprise a driver handle fixed to the opposite end of the coupling end. Thereby, rotation of the inserted screwing stylet can be facilitated via the driver handle.

According to an eleventh option of the first or second aspect, which can be combined with any of the first to tenth options, the driver handle of the screwing stylet may further comprise an annular opening surrounding the screwing stylet and configured to accommodate an end portion of a connector of the lead device. Thereby, the screwing stylet with the integrated driver handle can be easily fixed to the lead device by simply continuing the insertion process until the end portion of the connector of the lead device has been inserted into the driver handle.

According to a twelfth option of the first or second aspect, which can be combined with any of the first to eleventh options, the driver handle of the screwing stylet may further comprise a locking element for fixing the end portion of the connector of the lead device within the annular opening to the screwing stylet. Thereby, a fast and easy locking mechanism can be provided, where the locking element is simply activated for locking when the end portion of the connector of the lead device has been inserted into the driver handle. Of course, alternative locking mechanisms via bolt and hole or threaded portions on driver handle and end portion can be provided.

According to a thirteenth option of the first or second aspect, which can be combined with any of the first to twelfth options, the locking element of the driver handle of the screwing stylet may be configured to be connectable to a signal analyzer via a cable for signal transmission from the coupling end to the signal analyzer. Thus, the physician may easily connect the lead device with inserted screwing stylet to a signal analyzer to support the placement process.

According to an fourteenth option of the first or second aspect, which can be combined with any of the first to thirteenth options, the screwing stylet may further comprise an end portion protruding from the driver handle, to which a signal analyzer can be rotatably connected via a cable for signal transmission from the coupling end to the signal analyzer. Thus, a cost-saving “in line” connection with a rotating/sliding electrical connection around the stylet body, e.g., via a crocodile clamp, can be achieved to facilitate rotative operation for torque transfer.

It shall be understood that the lead device of claim 1 and the lead system of claim 8 may have similar and/or identical preferred embodiments, in particular, as defined in the dependent claims.

It shall further be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Various embodiments of the present invention are now described based on an improved lead system structure with lead device (e.g., electrode catheter) and insertable screwing stylet. Although the present invention is particularly advantageous within the context of transseptal pacing such as LBBP, the invention is not limited thereto and may also be used in connection with other pacing types and/or sites for other applications which require placement of a lead device.

It is noted that throughout the present disclosure only those blocks, components and/or devices that are relevant for the proposed lead system structure and placement operation are shown in the accompanying drawings. Other blocks have been omitted for reasons of brevity. Furthermore, components designated by same reference signs or numbers are intended to have the same or at least a similar function, so that their function is not described again later.

LBBP is defined as capture of the LBB (i.e., left bundle trunk or its proximal fascicles), usually with septal myocardium capture at low output (e.g., <1.0 V/0.4 ms).

Figure 1:
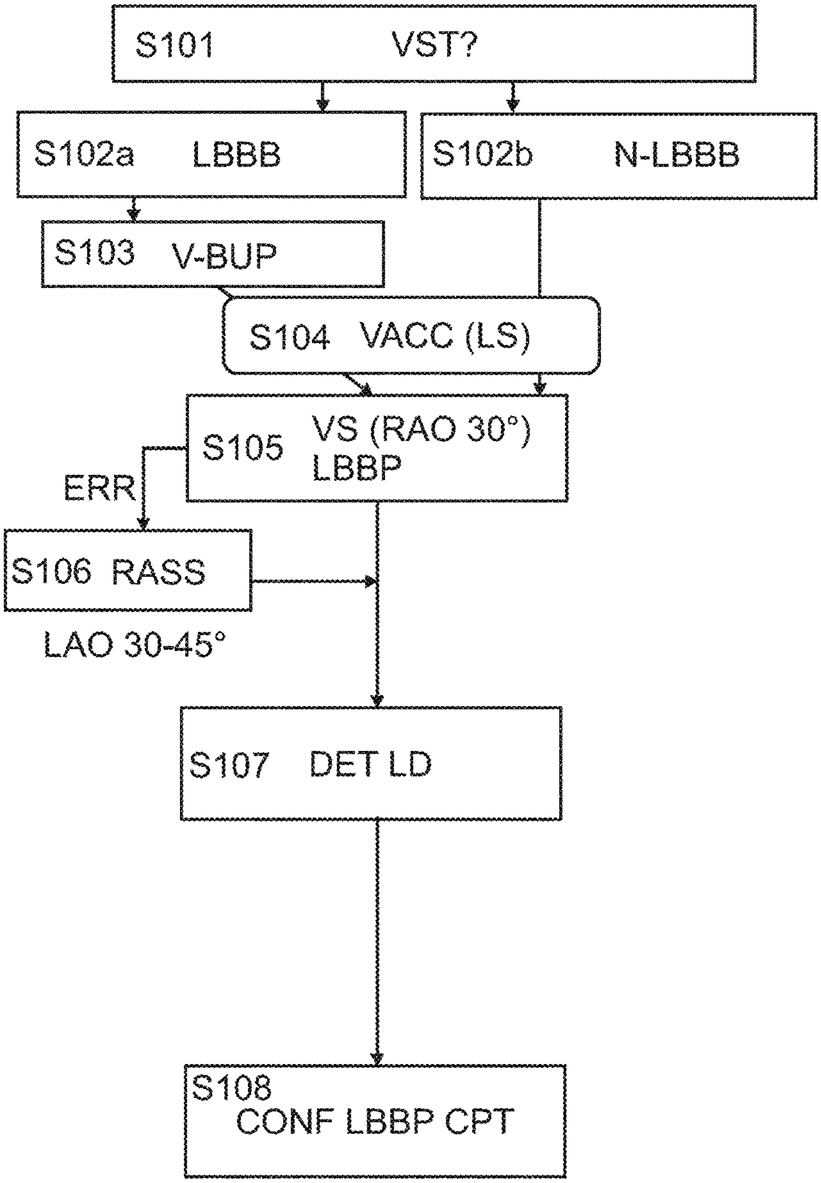
FIG. 1 shows schematically a flow diagram of a procedure for placement of an LBBP lead device according to various embodiments.

FIG. 1 shows a flowchart of an exemplary procedure for placing or implantation of a lead device for LBBP.

In a first step S101 ("VST?"), the ventricular septal thickness is assessed by echo and/or scar measurements. The IVS separates the LV and the RV and has an important role in the function of both ventricles. In an example, echocardiographic measurements may be used for measuring the septal thickness e.g. from the most distinct echoes including right and left endocardial surfaces at end diastole, which may be determined by the peak of the R wave of a simultaneously recorded ECG.

Based on an intrinsic rhythm of the heart derived from ECG measurements, presence or absence of LBBB is determined in steps S102*a* ("LBBB") or S102*b* ("N-LBBB"), respectively. LBBB completely modifies the electrical activation of the LV and QRS complex on the ECG. The activation of the septum, which is left-sided in physiologic conditions, originates on its right side. The electrical impulse propagates then inferiorly, to the left, and slightly anteriorly. This results in a nonhomogeneous and delayed depolarization of the LV.

The ECG criteria for an LBBB may include at least one of QRS duration greater than 120 ms, absence of Q wave in leads I, V5 and V6, monomorphic R wave in leads I, V5 and V6, and ST and T wave displacement opposite to the major deflection of the QRS complex.

A simple way to diagnose an LBBB in an ECG with a widened QRS complex (>120 ms) may be to look at lead V1. If the QRS complex is widened and downwardly deflected in lead V1, an LBBB is present. If the QRS complex is widened and upwardly deflected in lead V1, an RBBB is present.

If an LBBB has been determined in step S102*a*, an additional ventricular back-up pacing is added in step S103 ("V-BUP").

In both cases with or without LBBB, a vein access is performed from the left side via a lead device in step S104 ("VACC (LS)").

Then, an initial site for an LBBP location at the right surface of the ventricular septum (e.g., with RAO) 30° is determined in step S105 ("VS (LAO) 30° LBBP"). This may be achieved by placing the catheter about 1 to 1.5 cm from the HBP site towards the RVA and/or by using the paced morphology, where a "W" pattern with a notch closer to nadir (deepest point of the QRS signal) in lead V1 may indicate an ideal location. The pacing lead (e.g., helical electrode) is then screwed perpendicular into the LV septum (with LAO) 30-45°.

If an error ("ERR") is determined in step S105 due to a failure of fixation, a reassessment is initiated in step S106 ("RASS")

Then, in step S107 ("DET LD"), the LBBP lead depth into ventricular septum is determined. This can be achieved by at least one of observing changes in the notch in V1 lead, sheath angiography, fulcrum sign, and impedance monitoring.

The pacing lead is slowly turned into a depth of approximately 6 to 8 mm and/or based on an RBBB paced morphology while avoiding any perforation of the septum.

Finally, in step S108 ("CONF LBBP CPT"), LBB capture is confirmed based on acceptable pacing parameters. The confirmation may be based on at least one of a paced morphology of an RBBB pattern, a recording of an LBB potential, a stimulus-peak of the LVAT that shortens abruptly with increasing output or remains shortest and constant at low and high outputs, a selective LBBP and a non-selective LBBP, and a recording of a retrograde His potential or anterograde LBB potential during pacing.

To summarize, common features of the implantation or placement process include transvenous access, transseptal placement of the pacing lead into the LV septal subendocardium in the LBB region, and confirmation of capture of the LBB.

In case of an RBBB, when the pacing lead is placed transseptally from the RV septum to the LV septal subendocardium in the LBB region, the paced QRS morphology of the electrocardiogram (ECG) changes from an LBBB to a right bundle branch block (RBBB) pattern, as the LV is activated earlier than the RV. However, the paced morphology could be influenced by the pacing site of the LBB, existing bundle disease, or selective or nonselective LBB capture.

Figure 2:
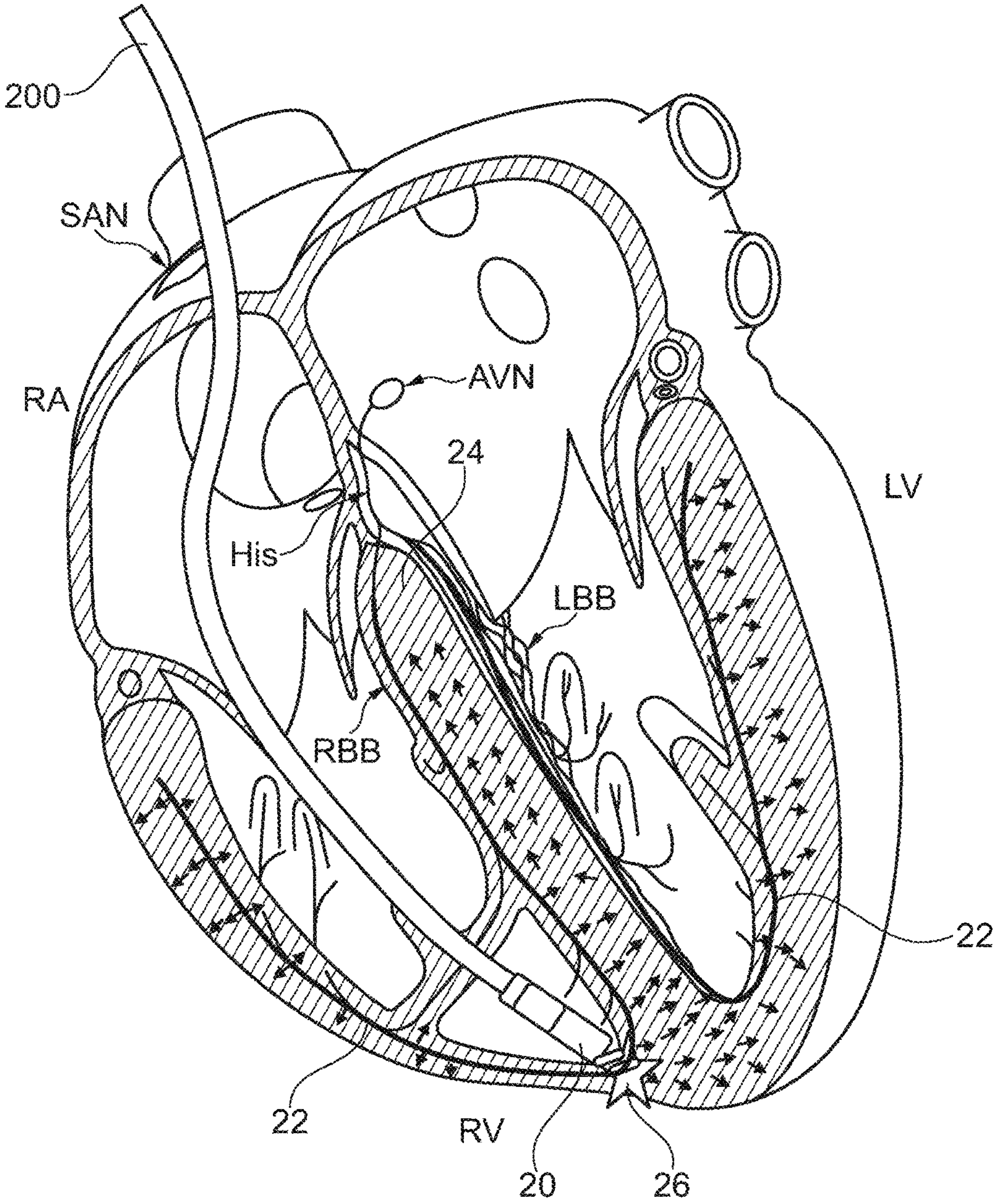
FIG. 2 shows schematically a heart with a lead device placed for RVA pacing.

FIG. 2 shows schematically a heart with a lead device placed for RVA pacing.

In a normal cardiac function, the heartbeat starts in the heart itself due to the SAN which is found in the top of the RA and sets the rate at which the heart contracts. It sends out electrical impulses which are carried through the muscular walls of both atria. These impulses cause atrial systole. The impulse is then passed to another node within the heart—the AVN. This node is in the lower part of the RA. Once the impulse from the SAN reaches the AVN the impulse is passed to conducting fibers which travel down the central wall of the heart. The impulse then splits and travels up the LV and RV causing them to contract simultaneously (ventricular systole).

Important elements of the conduction system of the heart are found within the septum (IVS) 24. The His bundle travels in the subendocardium, down the right side of the septum 24 for about 1 cm before dividing into the LBB and RBB. The LBB continues down the right side of the septum 24, while the LBB crosses to the left side and splits into anterior and posterior divisions.

Under normal circumstances, excitation from the SAN controls the heart rhythm. An abnormality in the sinus rhythm leads to arrhythmia, which refers to abnormalities in the rate, rhythm, site of origin, and conduction of the cardiac electrical pulse. When disorders occur in specific intraventricular conduction fibers, the repolarization wave must travel through the slower muscle-muscle conduction to reach the ventricles. Classic disorders related to conditions that involve different conduction bundle branches include LBBB and RBBB. An ECG can be used to measure and record cardiac electrical activities and thus can provide important information on cardiac functions. The ECG has been used as a standard diagnostic tool to analyze arrhythmia.

RVA pacing 26 via a lead device 200 including a pacing lead 20 causes abnormal contraction patterns and a consequent dyssynchrony of LV free wall and septum 24 may cause myocardial perfusion defects, histopathological alterations, left ventricular dilation and both systolic and diastolic left ventricular dysfunction. All these long-term changes could account for higher morbidity and mortality rates observe in patients with chronic RVA pacing 26 compared with atrial pacing.

Two different electrical activation speeds through the heart can be observed. These are a first activation speed (low speed conduction/contraction) via myocytes (i.e., muscle cells) indicated as small arrows in FIG. 2 and a second activation speed (high speed conduction) via Purkinje fibers 22 (i.e., subendocardial branches) wherein the second speed is about ten times as high as the first speed. Thus, Purkinje fibers 22 can be seen as a kind of stimulation "highway".

Figure 3:
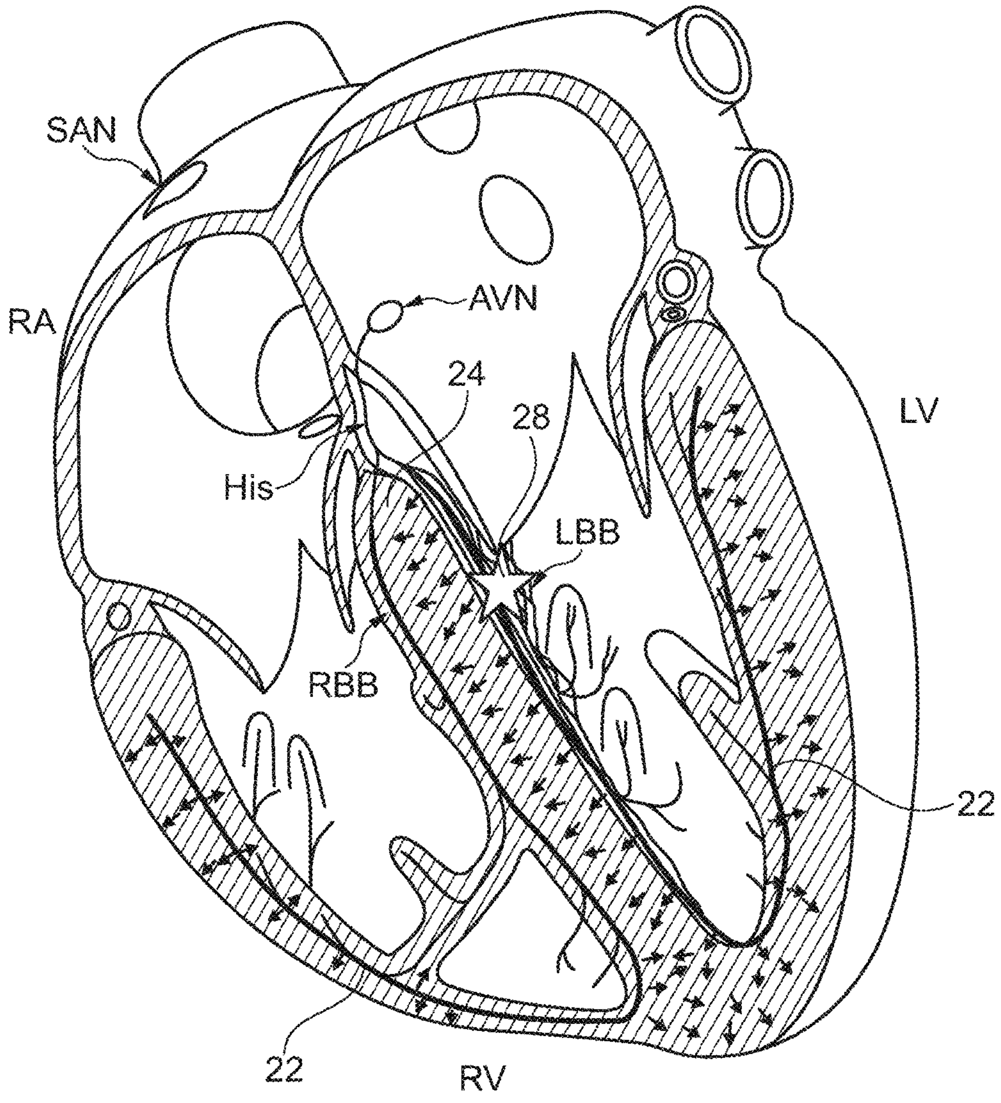
FIG. 3 shows schematically a heart with an indication of an LBB pacing site.

FIG. 3 shows schematically a heart with an indication of an LBB pacing site 28.

The LBB pacing site 28 is located at the Purkinje fibers 22 of the LV and thus activates a more physiologic contraction by providing synchrony of the LV free wall and septum 24.

Figure 4:
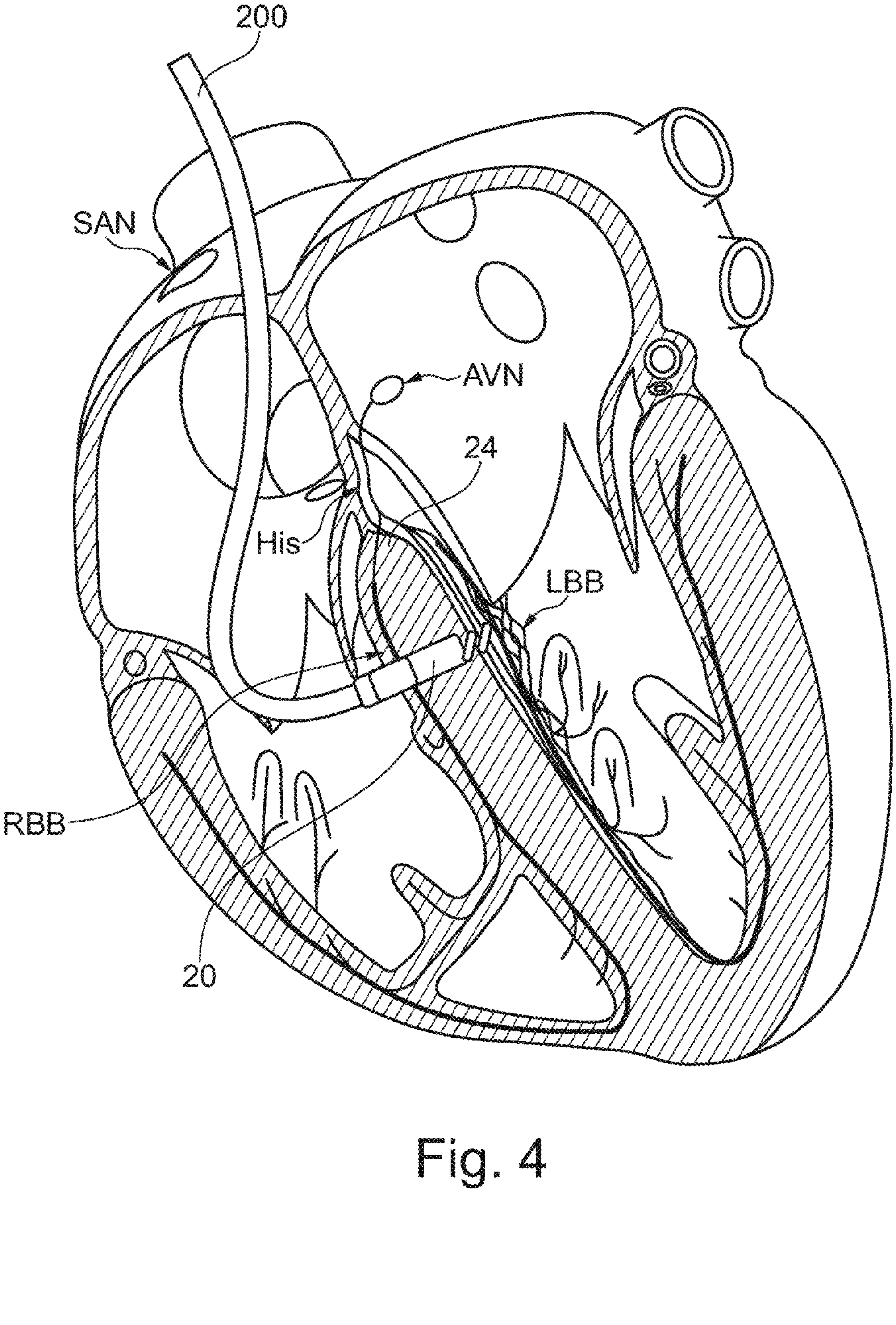
FIG. 4 shows schematically a heart with a lead device placed for ventricular transseptal LBB pacing.

FIG. 4 shows schematically a heart with an inserted lead device 200, where the pacing lead 20 is placed for ventricular transseptal LBBP. The placement of the pacing lead 20 may be performed based on the procedure explained above in connection with FIG. 1.

Thereby, the LV is paced from the RV by a ventricular transeptal approach as a guide for catheter delivery.

The following embodiments of the proposed lead system are configured to minimize the impact of lead device insertion through the septum 24 (e.g., to prevent permanent damages of arteries) by downsizing of the puncturing area, provide enhanced control over the puncturing process by an improved torque transfer mechanism with insertable screwing stylet, and ensure long term reliability of the lead device exposed to contraction constrains of the septum 24 by providing a small and robust structure and/or continuous flexibility.

The body of the lead device can be configured to improve slipperiness of a contact with a guiding catheter used for guiding the lead device (e.g., through a blood vessel) to a target area. This can be achieved by using e.g. a polyurethane (PU) material with reduced diameter to allow an advancement progress of the lead body through the guiding catheter and the lead tip through the septum 24 with limited effort.

Suitable designs of the lead device may have a multi-lumen, coaxial and coradial structure, both as tachycardia leads or bradycardia leads, as long as a central lumen for a stylet passage is provided. Coaxial leads have an inner conductor that extends down the length of the lead to the tip electrode, the cathode, arranged in a coil configuration with a central lumen to allow for passage of a stylet at implantation. This coil may be covered by a cylindrical length of inner insulation, which in turn may be wrapped by another coil conductor that also runs down the lead to the ring electrode, the anode. A second, outer layer of insulation and lead covering protect the ring conductor from the outside environment, thereby completing the design. Coradial bipolar leads address some concerns of coaxial leads with respect to bulk and stiffness of the four-layer design by providing a new conductor and insulator technology where a single coil extends down the length of the lead (again with a central lumen to allow for stylet insertion) and consists of two or four parallel, alternating insulated conductor strands, one or two of which connects to the cathode and the other one or two to the anode. Each conductor strand may be individually coated with a bonded layer of e.g. ethylene tetrafluoroethylene (ETFE) fluoropolymer insulation which serves to insulate each strand from the other, despite being intertwined. The single, two-component coil may be surrounded by a single, outer insulation covering.

The multi-lumen or coaxial or coradial leads may optionally comprise a fixed, nonretractable helix to minimize size. However, a retractable helix may as well be used in connection with the described embodiments.

Furthermore, the proposed lead system may be configured to provide improved torquability, i.e., an ability to transmit safely torque to the helix (e.g., full lead body torque) and stylet-driven compatibility to ease the handling (e.g., by push transmission). In an example, a coradial lead with compatible screwing stylet (screwdriver stylet) may be provided, as described later.

As regards the design of the distal end (distality) of the lead device, the ratio between the outer diameter of the helix and the outer diameter of the housing should be larger than 80%, wherein an isoprofil distality may be provided to avoid a front stop surface.

Furthermore, a rigid helix may be provided to avoid deformation of the helix during screwing (e.g., 30M helix design), while a fixed helix (i.e., a lock between helix and lead body) may simplify handling (i.e., no parasite tool is required for a retractable system).

Moreover, design flexibility may be provided by adapting an inter-electrode distance for both side pacing to different thicknesses of the septum 24.

The distal design of the lead device may further be configured to allow smooth and predictable advancement of the lead tip into the septum 24 until the helix (cathode) reaches the desired location at the LV chamber, i.e., close to the LBB without full perforation of the septum 24, so that the helix does not protrude into the LV chamber.

Additionally, the design of the lead device may be configured to minimize the required energy to perform the puncturing of the septum 24. This may be achieved by providing a dedicated distally tapered tip with a conical shape e.g. for the inter-electrode section (between distal helix end and proximal anode end).

In the following, various embodiments of the proposed lead system with lead device and separate insertable screwing stylet are described with reference to FIGS. 5 to 9 and 11.

Figure 5:
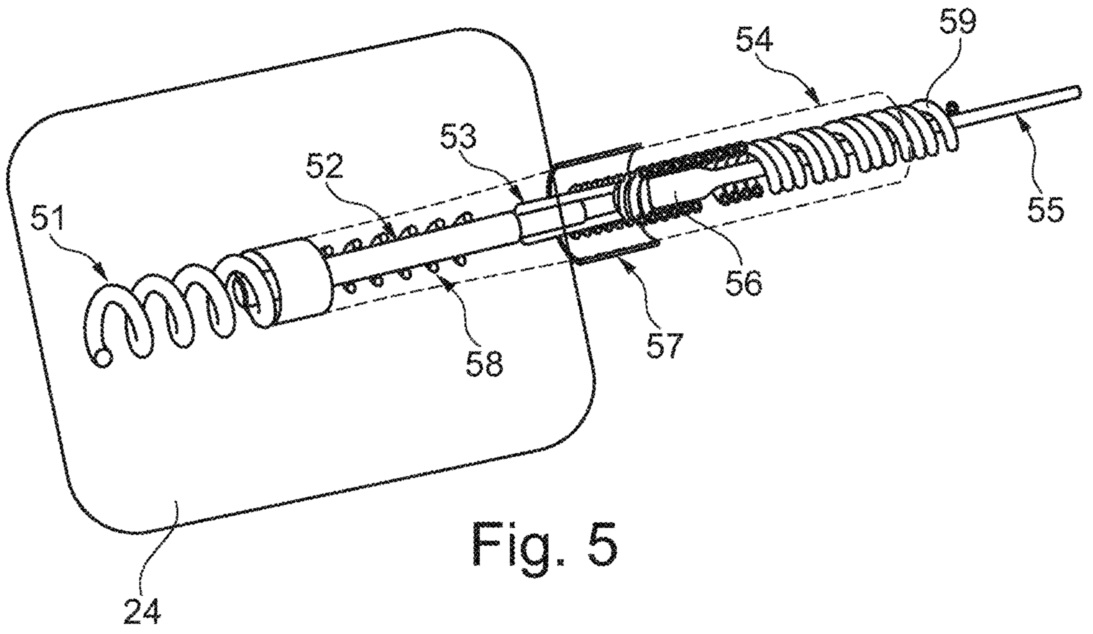
FIG. 5 shows schematically a lead device according to an embodiment.

FIG. 5 shows schematically a partially disassembled lead system (screwing stylet 55 not yet fully inserted) according to an embodiment which is partially introduce into the septum 24 according to a desired depth required e.g. for LBBP.

The proposed lead system comprises a helix 51 that is mounted (e.g., welded) on a driver 52 which may comprise a surrounding inner coil 58 or other non-flat regular or irregular surface structure to ensure a good adhesion of the surrounding material of the lead body 54 to the driver 52 at the interelectrode portion to thereby obtain a simple rigid and durable structure of the lead tip with low number of components for improved long-term reliability. The driver 52 is fixedly supported in a lead body 54 and mechanically and electrically connected to a screwing stylet adapter 53 matched for insertion of a coupling end (engagement portion) 56 of the separate screwing stylet 55 with a screwdriver function for allowing rotational driving of the helix 51 via the driver 52. Due to the electrical connection between the helix 51 and the screwing stylet 55, electrical signals sensed by the helix 51 at the target area can be routed via the screwing stylet 55 to a signal analyzer and used for monitoring correct placement of the helix 51 during the screwing operation without any disconnection of e.g. a crocodile clamp allowing a single step operation (no more sequence of screwing, clamp connecting, electrical measurement, clamp disconnecting, additional screwing, clamp connecting etc.).

Typical dimensions of the screwing stylet 55 may be a nominal diameter in the range of 0.30 mm to 0.50 mm, a reduced diameter between 0.10 mm and 0.25 mm at a distal portion to enhance flexibility, and a length of the reduced diameter between 0 mm to 200 mm. The screwing stylet may be made of stainless steel (e.g., a classic inox 304 or 306 for a standard version) or a highly elastic material such as Nitinol which is more efficient and robust to sustain torque constrains and avoid any risk of breakage in use.

In FIG. 5, the screwing stylet 55 is not yet fully inserted into and engaged with the adapter 53 of the driver 52.

The adapter 53 may be an integral part of the driver 52 or may be removably or non-removably fixed to the driver 52 to allow for adaptation to different types of screwing stylets 55 with different shapes or dimensions of their coupling ends 56.

In the present embodiment, the coupling end 56 of the screwing stylet comprises a flat shape (similar to a screwdriver). The adapter 53 comprises a mating part (e.g., matching slot or recess) for accommodating the coupling end 56 of the screwing stylet 55.

More general, the coupling end 56 of the screwing stylet 55 may comprise one of a plurality of cavities or protrusions that allow torque to be applied to the mating part of the driver 52. Examples are slotted drive types, cruciform drive types, square dive types, multi-square drive types, internal hex drive types, pentalobular drive types, hexalobular (Torx) drive types, combination (plus-minus) drive types, external drive types, or tamper-resistant drive types.

The proposed configuration of the lead system with the driver 52, the optional adapter 53 and the screwing stylet 55 optimizes torque transfer from a physician's hand to the helix 51 and minimizes friction of the lead body 54 within a guiding catheter during placement.

Furthermore, the lead body 54 comprises an anode 57 and an optional conical interelectrode portion between the helix 51 (cathode) and the anode 57. Electric signals (e.g., pacing signals) to the helix 51 and the anode 57 are transferred along the lead device in a respective coated wiring 59. In the example shown in FIG. 5, two insulated wires are used for each electrode (i.e., anode 57 and cathode at the helix 51).

The coradial structure of the lead device of FIG. 5 allows a combination of a lead body 54 with reduced size (e.g., 4.8F) and a PU insulation. Furthermore, a simple and robust structure with minimal number of components can be provided to minimize stiffness gradients and number of welding, and/or glueing portions or other weak junction points. The insulation plastic material surrounding the rigid driver 52 may be reflowed onto the driver 52 so that no residual gap remains between these two elements which are exposed to high level of septum compression. Thereby, local flexion stresses and a resulting risk of plastic cracks over time can be prevented.

Figure 6:
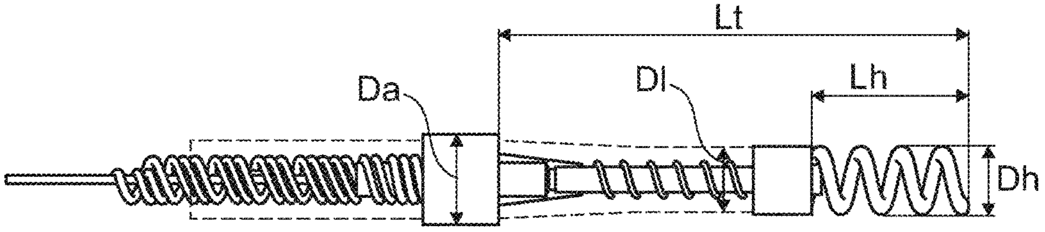
FIG. 6 shows schematically a lead device according to the embodiment with indicated dimension parameters.

FIG. 6 shows schematically the lead system of FIG. 5 with fully inserted screwing stylet 55 and indicated dimensional parameters of an outer diameter DI of a distal end of the lead housing at the helix 51, an outer diameter Dh of the helix 51, an outer diameter Da of the proximal welding anode 57, a length Lh of the helix 51, and a total length Lt of the lead tip including the distal helix 51 and a tapered or conical portion of the lead body 54 surrounding the driver 52 between the helix 51 and the proximal anode 57.

The ratio Dh/DI can be set between 0.8 and 1, while Dh can be set between 1 and 1.8 mm (preferably 1.40 mm), Da can be set between 1.25 mm and 1.94 mm (preferably 1.66 mm), Lt can be set between 8 and 15 mm, and Lh can be set between 1.5 and 5 mm.

This proposed specific conical shape with the above mentioned ranges of dimension ensures that the lead tip with the helix 51 can be used to puncture tissue in the target area in a controlled and smooth manner.

Figure 7:
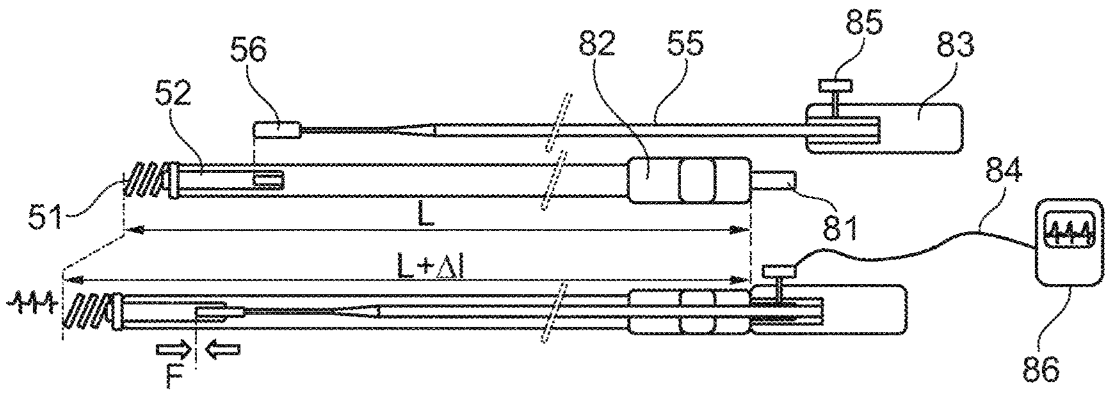
FIG. 7 shows schematically disassembled and assembled portions of a lead device according to an embodiment.

FIG. 7 shows schematically a disassembled and assembled lead system with a screwing stylet 55 with integrated operating handle (screwdriver handle) 83 according to an embodiment.

In FIG. 7, the upper part shows the separate screwing stylet 55 with integrated operating handle 83 and locking element (e.g., a metal lateral locking screw) 85 for fixing the screwing stylet 55 to a hollow end portion 81 of a connector (e.g., an IS1 connector) 82 of the lead device. The screwing stylet 55 may comprise at its distal end a conical portion with decreasing diameter followed by a flexible portion with constant small diameter and a flat-shaped coupling end 56 to be coupled to a driver 52 of the lead device.

In the middle part of FIG. 7, the lead device with a helix 51, the driver 52 with integrated mating portion for inserting the coupling end 56 of the screwing stylet 55, the connector 82 and its end portion 81 is shown.

Finally, in the lower part of FIG. 7, the assembled lead system with lead device and inserted and coupled screwing stylet 55 is shown, where the helix 51 is correctly placed for LBBP and thus receives a ORS signal from the LBB. The screwing stylet 55 has been inserted through the hollow end portion 81 of the connector 82 of the catheter and coupled to the driver 52, while the end portion 81 of the connector 82 has now been inserted into an annular opening of the integrated operating handle 83 that surrounds the screwing stylet 55 and has been fixed via the locking element 85.

In the embodiment of FIG. 7, a signal analyzer 86 can be connected via a cable (e.g., a pacing system analyzer (PSA) cable) 84 to the locking element 85 which is electrically coupled to the screwing stylet 55 via the end portion 81 of the connector 82 of the catheter.

The QRS signal from the LBB can thereby be routed through the helix 51, the driver 52, the screwing stylet 55, the locking element 85 and the PSA cable 84 to the signal analyzer 86 which can be used for monitoring proper placement of the lead device during puncturing.

It is noted that in FIG. 7 schematic functional components are only shown, while the wiring for pacing signals and the lead tip with its shape and anode has been omitted for brevity reasons.

As indicated in FIG. 7, the lead body of the lead device may be configured to allow an elastic elongation L+ΔI (e.g., ΔI=1 to 10 mm) in response to a force applied to the lead body. The resulting axial elasticity of the connection system generates a compression force F that ensures stable and reliable engagement of the flat coupling end 56 of the screwing stylet 55 into the driver 52 during the placement procedure and despite numerous constrains (traction, push, torque, flexion etc.) related to the puncturing process. It also secures temporary electrical connection between the driver 52 and the screwing stylet 55 to reduce artefacts or other interferences in electrical signals transferred to the signal analyzer 86.

The integrated operating handle 83 provides a simple "hands free" locking handle for operating the lead device to achieve an improved torque transfer from a physician's hand to the helix 51 via the screwing stylet 55 and the driver 52.

The non-retractable fixed helix 51 facilitates handling of the lead device, as no dedicated tool for the retracting mechanism with associated risk of mishandling is required.

The screwing stylet 55 (which can be provided as a separate adaptive accessory for the lead device) provides a screwdriver functionality for transmission of an increased torque for the challenging puncture process. The screwing stylet 55 engages directly with the driver 52 at the tip of the lead and thereby allows a direct and efficient torque transfer to the fixed helix 51. This proposed arrangement also minimize any stresses applied to the internal structure of the lead device (e.g., by glueing and/or welding portions or the like) during puncture.

The material and design of the screwing stylet 55 can be selected to achieve high flexibility at the last 10 cm prior to the coupling end 56 (e.g., via a conical and/or reduced diameter portion) so as to easily pass through the two curves of the guiding catheter within the heart to avoid any risk of tip dislodgment from the target area during insertion of the screwing stylet 55. Moreover, a high torque transmission (higher than the lead body) can be achieved despite reduced distal diameter and a “hands free” simple locking and operating handle 83 is provided to engage the distal coupling end (e.g., flat end) 56 of the screwing stylet 55 into the mating part (e.g., receptacle) at the driver 52 (or adapter 53) for the screwing operation.

Figure 8:
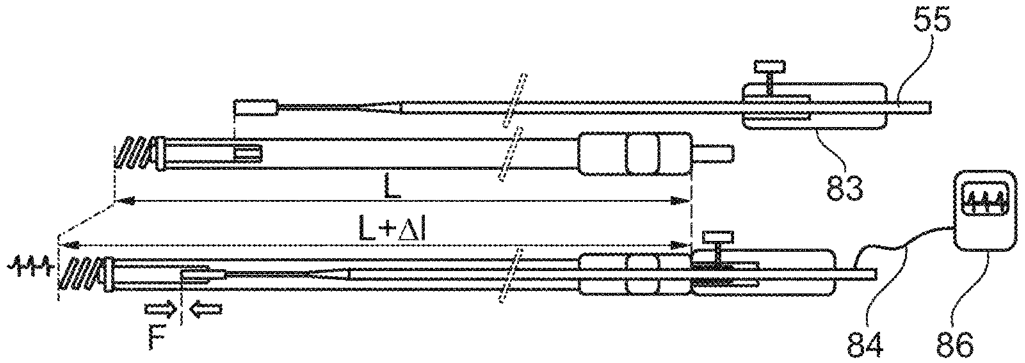
FIG. 8 shows schematically disassembled and assembled portions of a lead device according to an embodiment with modified signal tap.

FIG. 8 shows schematically disassembled and assembled portions of a lead device according to an embodiment with modified signal tap provided by a screwing stylet 55 with lock, torque and map function.

Similar to FIG. 7, only schematic functional components are shown in FIG. 8, while the wiring for pacing signals and the lead tip with its shape and anode has been omitted for brevity reasons.

Here, the operating handle 83 is modified so that an end portion of the screwing stylet 55 protrudes from the operating handle 83 and can be used for connecting the signal analyzer 86 via the cable 84, e.g., a PSA cable.

Thus, body of the screwing stylet 55 goes straight through the operating handle 83 to achieve a cost-saving “in line” connection with an option for a rotating/sliding electrical connection around the stylet body, e.g., via a crocodile clamp on the cable 84.

Figure 9:
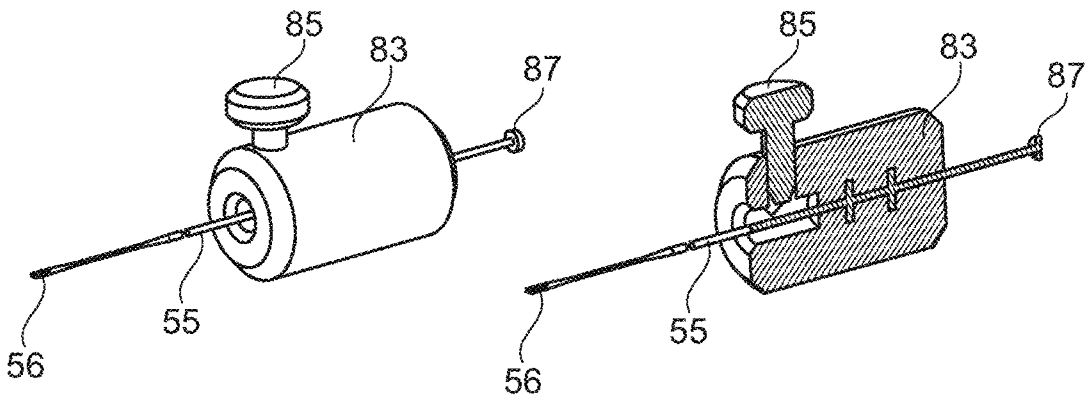
FIG. 9 shows schematically a side view and cross-sectional view of a driver handle of a screwdriver stylet of the lead device according to an embodiment.

FIG. 9 shows schematically an oblique view (left part) and cross-sectional view (right part) of the operating handle 83 of the screwing stylet 55 of the lead device according to an embodiment.

The wire or body of the screwing stylet 55 with its flat coupling end 56 is fixed to the operating handle 83 (by molding or the like) and locked in translation and rotation. The lateral locking element 85 can be used to temporary connect/lock the operating handle 83 onto the end portion (not shown) of the connector (e.g., IS1 connector pin) of the lead device. The protruding end portion of the screwing stylet 55 comprises a connecting end 87 for connecting a cable to a signal analyzer or the like.

A physician may thus place the lead device into the target area e.g. by first inserting the lead device without the screwing stylet 55 e.g. through a blood vessel via e.g. a guiding catheter until the helix 51 reaches the target area. Then, the physician may insert the screwing stylet 55 until it engages with the driver 52 and may push the operating handle 83 fixed to the screwing stylet 55 at the connector end opposite to the coupling end 56 to generate a connecting force between the coupling end 56 of the screwing stylet 55 and the driver 52 due to the elastic elongation of the lead body 54 of the lead device. The physician may then lock this position of the operating handle 83 to the lead body 54 by using the locking element 85 of the operating handle 83 to maintain the connecting force and may then turn the operating handle 83 (or the connector 82) to screw the helix 51 into the target area (e.g., septum). He/she may further use the temporary electrical connection through the screwing stylet 55 to catch the electrical sensing (e.g., QRS signal) at the helix level and identify when the helix 51 engages the LBB or another target location. This allows an easy one-hand (“hands free”) placing procedure of the helix 51 via the operating handle 83 (or the connector 82).

Thus, the proposed two-component lead system can be configured to temporarily fix or lock both ends of the assembled lead device and screwing stylet 55, wherein the distal flat end (coupling end 56) of the screwing stylet 55 engages with the mating portion of the driver 52 under a predefined force determined by the elastic elongation of the lead body 54. Thereby, an important temporary increase of the torque transfer together with increased operating comfort during the critical screwing operation for placement of the lead device can be achieved. Both lead device and screwing stylet 55 can be temporarily operated as a single device to release one hand of the physician.

Figure 10:
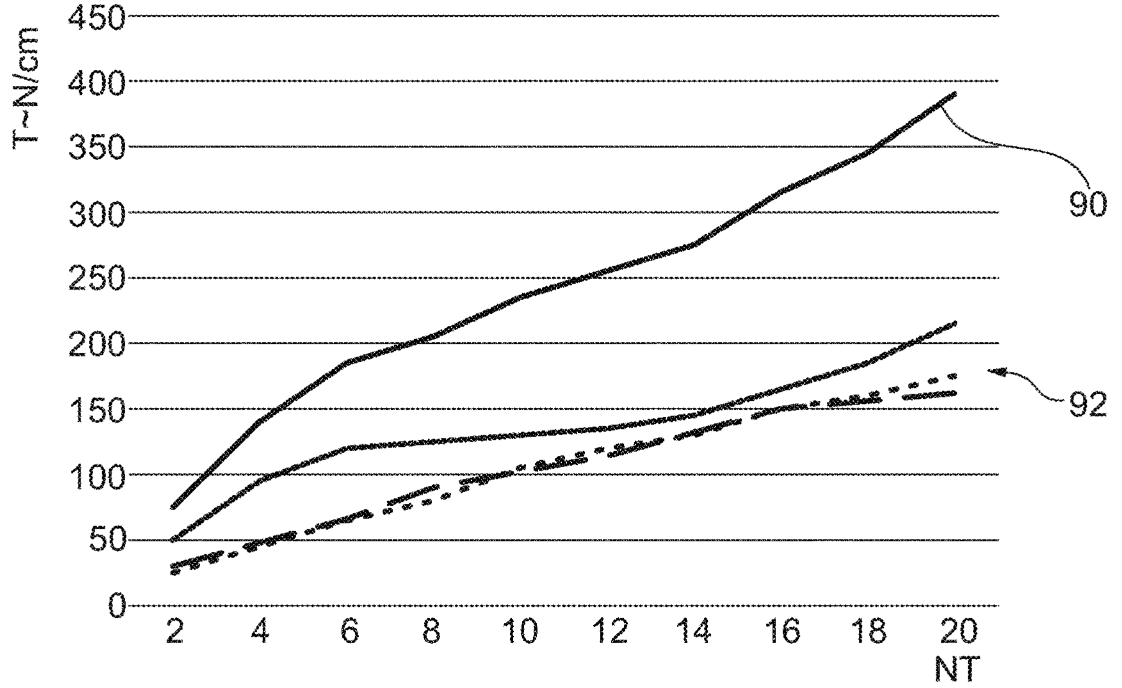
FIG. 10 shows a diagram of an achieved lead torque versus number of lead turns for a lead device according to an embodiment in comparison to conventional lead devices.

FIG. 10 shows a diagram of an achieved lead torque versus a number of lead turns for a lead system according to an embodiment in comparison to conventional lead devices.

The diagram shows an improved torque curve 90 achieved by the proposed lead system with screwing stylet and driver handle in comparison with a group 92 of torque curves achieved by conventional lead devices and screwing stylet only.

More specifically, the improved torque curve 90 corresponds to the sum of the most upper curve of the group 92 (which corresponds to the screwing stylet only) and the curve of the lead device only (one of the lower curves of the group 92). Although the screwing stylet alone provides better torque transfer (about 10% to 20% increase), the sum of both screwing stylet and lead body leads to a 100% increase in torque versus the lead device alone. Therefore, the temporary connection of both components (screwing stylet and lead device) of the proposed lead system during placement of the lead device substantially improves torque transfer and ease of use for a physician. To achieve the same performance without temporary connection of the two components, the physician would have to turn both devices at the same time with the same speed, which is quite impossible considering that he/she has to take care of many other things at this crucial step (e.g., analyzer signal, patient parameters etc.).

As can be gathered from the diagram of FIG. 10, the improved torque curve 90 shows a fairly steady increase of the lead torque with increasing number of turns, which facilitates smooth and predictable advancement of the helix of the lead device into the septum or other target areas.

Figure 11:
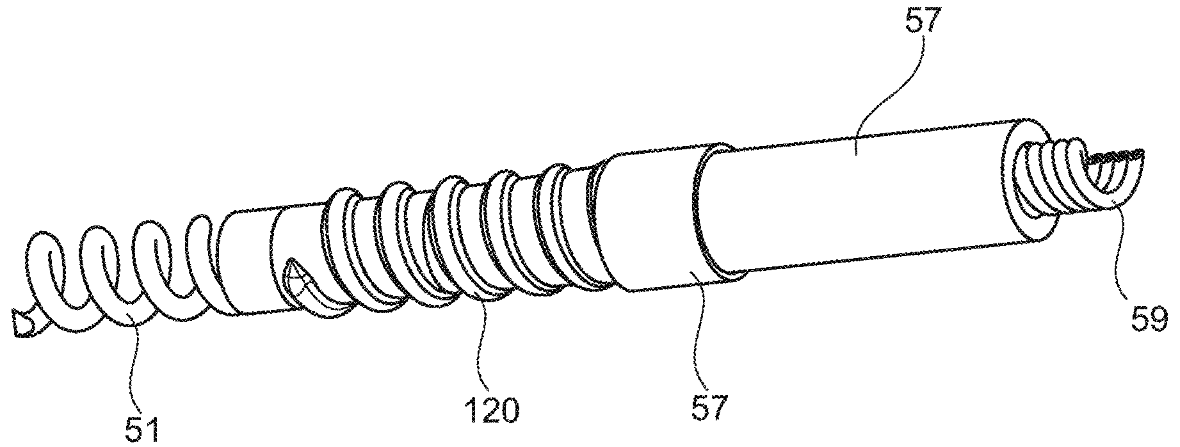
FIG. 11 shows schematically a lead device with molded screw structure according to an embodiment.

FIG. 11 shows a lead device with a screw structure 120 that has been molded or otherwise formed on or attached to the outer surface of the inter-electrode portion of the lead body 54 between the helix 51 and the welding anode 57. The screw structure 120 may be made of a plastic material (e.g., PU). The pitch of the windings of the screw structure may substantially correspond to the pitch of the helix 51 to allow a smooth insertion of the interelectrode portion after the helix 51 during puncturing of the tissue at the target area (e.g., the septum) for LBBP.

Moreover, the lead device with the screw structure 120 can be used with or without the screwing stylet explained above in connection with other embodiments. In the first case, the lead device of FIG. 11 includes the driver which can be coupled to the screwing stylet.

It is noted that the dimensions of the tip of the lead device of FIG. 11 and of the other lead devices of FIGS. 7 and 8 may correspond to those indicated in FIG. 6.

To summarize, a lead device with improved puncturing capability and reliability has been described. The proposed structure, shape and dimensions of a tip of the lead device are configured to enable a controlled and smooth puncturing process through the septum or other tissue at the target area with high reliability and longevity. A fixed helix is provided to facilitate handling and an additional screwing stylet with screwdriver functionality may be provided to improve torque transfer to the tip of the lead device for better control of a puncturing process.

While the invention has been illustrated and described in detail in the drawings and foregoing description, such illustration and description are to be considered illustrative or exemplary and not restrictive. The invention is not limited to the disclosed embodiments. It can be applied to various types of lead devices (e.g., bradycardia or tachycardia lead devices with multi-lumen, coaxial or coradial structure) and applications in the field of cardiac pacing or sensing systems. Furthermore, the screwing stylet may be provided as an integrated component of the lead device that is no removable from the lead body.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. The foregoing description details certain embodiments of the invention. It will be appreciated, however, that no matter how detailed the foregoing appears in the text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A lead system comprising:

an insertable screwing stylet having a coupling end; and a lead device including:

a lead body; and a lead tip comprising a fixed distal helix as a first electrode and an interelectrode portion between the helix and a proximal second electrode;

wherein a ratio between a first outer diameter of the helix and a second outer diameter at a distal end of the interelectrode portion is set between 0.8 and 1, the first outer diameter is set between 1 and 1.8 mm, the length of the lead tip is set between 8 and 15 mm, and the length of the helix is set between 1.5 and 5 mm;

wherein the lead tip further comprises an integrated driver adapted to be coupleable to the coupling end of the insertable screwing stylet, wherein the helix is configured to receive a torque by means of the screwing stylet via the driver;

wherein the screwing stylet is configured to be insertable into the lead device and coupleable to the driver via the coupling end in order to transfer a torque to the helix;

wherein the screwing stylet further comprises a driver handle fixed to the opposite end of the coupling end;

wherein the driver handle comprises an annular opening surrounding the screwing stylet and configured to accommodate an end portion of a connector of the lead device.

2. The lead system of claim 1, wherein the interelectrode portion has a conical shape.

3. The lead system of claim 1, wherein the lead body has a coradial structure.

4. The lead system of claim 1, wherein the interelectrode portion comprises a screw structure molded or otherwise formed on or attached to an outer surface of the interelectrode portion.

5. The lead system of claim 1, wherein a third outer diameter at the proximal second electrode is set between 1.25 mm and 1.94 mm.

6. The lead system of claim 1, wherein the driver comprises an adapter with a mating portion adapted to be coupleable to the coupling end of the insertable screwing stylet.

7. The lead system of claim 1, wherein the screwing stylet further comprises a conical portion and/or a reduced diameter portion at the coupling end to increase flexibility and limit a maximum transmittable torque to a given value.

8. The lead system of claim 1, wherein the lead device is configured to allow an elastic elongation of the lead body to generate a compression force to support engagement of the coupling end into the driver.

9. The lead system of claim 1, wherein the screwing stylet is made of Nitinol.

10. The lead system of claim 1, wherein the driver handle comprises a locking element for fixing the end portion of the connector of the lead device within the annular opening to the screwing stylet.

11. The lead system of claim 10, wherein the locking element is configured to be connectable to a signal analyzer via a cable for signal transmission from the coupling end to the signal analyzer.

12. The lead system of claim 1, wherein the screwing stylet further comprises an end portion protruding from the driver handle, to which a signal analyzer can be rotatably connected via a cable for signal transmission from the coupling end to the signal analyzer.

* * * * *